United States Patent [19]

Wagner

[11] 4,377,783

[45] Mar. 22, 1983

[54] MOISTURE DETECTOR

[76] Inventor: Delmer W. Wagner, 392 Pine Grove Rd., R.R., Rogue River, Oreg. 97537

[21] Appl. No.: 284,358

[22] Filed: Jul. 17, 1981

Related U.S. Application Data

[63] Continuation of Ser. No. 84,881, Oct. 15, 1979, which is a continuation-in-part of Ser. No. 25,768, Apr. 2, 1979, abandoned.

[51] Int. Cl.³ .......................................... G01R 27/26
[52] U.S. Cl. .................................................. 324/61 R
[58] Field of Search ........................... 324/61 R, 61 P; 34/16.5

[56] References Cited

U.S. PATENT DOCUMENTS

| | | |
|---|---|---|
| 2,950,436 | 8/1960 | Butticaz et al. ................... 324/61 R |
| 3,043,993 | 7/1962 | Maltby .......................... 324/61 R X |
| 3,209,247 | 9/1965 | Mead et al. ....................... 324/61 P |
| 3,339,137 | 8/1967 | Perry .............................. 324/61 R |
| 3,354,388 | 11/1967 | Perry ............................ 324/65 R |
| 3,430,357 | 3/1969 | Perry ............................... 34/16.5 |
| 3,448,381 | 6/1969 | Perry ............................. 324/61 R |
| 3,491,292 | 1/1970 | Evans ............................. 324/61 R |
| 3,515,987 | 6/1970 | Zurbrick et al. .................. 324/61 R |
| 3,523,243 | 8/1970 | Wagner ........................... 324/61 R |
| 3,523,246 | 8/1970 | Hall et al. ....................... 324/61 R |
| 3,593,128 | 7/1971 | Perry ............................. 324/61 R |
| 3,811,087 | 5/1974 | Schmeizer ..................... 324/61 P X |
| 3,959,723 | 5/1976 | Wagner ........................... 324/61 P |

FOREIGN PATENT DOCUMENTS

| | | | |
|---|---|---|---|
| 985743 | 3/1976 | Canada ............................ | 324/61 R |
| 271877 | 5/1971 | U.S.S.R. ......................... | 324/61 R |

Primary Examiner—Stanley T. Krawczewicz
Attorney, Agent, or Firm—Klarquist, Sparkman, Campbell, Leigh, Whinston & Dellett

[57] ABSTRACT

A moisture detector for plywood veneer receives veneer sheets from a dryer on a conveyor and suitably includes adjacently spaced transmitting and receiving plates. A transmitting plate extends the full width of the conveyor, and is supplied from a transformer winding with a high A.C. voltage which is thereby capacitively coupled to the veneer. Receiving plates are shielded and segmented, and are connected to separate detector circuits for operating veneer-marking sprayers when a receiving plate receives an A.C. signal of predetermined value indicative of moisture in the wood. Each detector circuit and receiving plate shield are returned to a first potential reference below conveyor ground level in common with the transformer winding return. Conveyor ground is connected to a tapped voltage divider disposed across the transformer winding whereby a conductive path is provided to the veneer, for example when the veneer becomes substantially shorted to the conveyor by moisture. The last mentioned conductive path can alternatively be employed for moisture detection even in the absence of a transmitting plate.

42 Claims, 6 Drawing Figures

MOISTURE DETECTOR

CROSS REFERENCE TO RELATED APPLICATION

This application is a continuation of application Ser. No. 084,881, filed Oct. 15, 1979, which is a continuation-in-part of application Ser. No. 025,768, filed Apr. 2, 1979, abandoned for Moisture Detector.

BACKGROUND OF THE INVENTION

The present invention relates to a moisture detector and particularly to a moisture detector adapted to detect moisture in plywood veneer with a minimum of apparatus, expense and complexity.

Some form of moisture detector is frequently employed at the outlet of a plywood veneer dryer so that wet pieces of veneer can be identified and redried. Many such devices employ conductive circuits, for example utilizing wire brushes which contact the veneer and register electrical conduction produced by moisture. Unfortunately, the wire brushes are subject to breakage and shorting whereby the moisture indications tend to become inaccurate. A more advantageous form of moisture detector is the non-contacting variety, for example employing capacitive plates spaced from the veneer which indicate moisture by coupling an A.C. signal between the capacitive plates and the veneer when the veneer is sufficiently wet. Some non-contacting devices are not particularly sensitive. A desirable configuration employs a transmitting plate adjacent the veneer, and a receiving plate offset along the path of the veneer for receiving an A.C. signal under moisture conditions. This type of moisture detector is exemplified by my U.S. Pat. No. 3,523,243, granted Aug. 4, 1970.

In a typical veneer handling installation, the strips or sheets of veneer are conveyed on a conveyor, e.g. including steel rollers which are ordinarily grounded to equipment ground and earth ground. When the veneer is extremely wet, the A.C. signal merely becomes shorted to ground via the conveyor rollers. Of course, a conveying system could be used which is essentially non-conductive, e.g. employing insulated rollers or the like, but this kind of insulation would involve extra expense. It might be thought a moisture detection system could be employed which is completely isolated electrically from its surroundings and therefore not subject to being grounded by the conveying equipment. However, an ungrounded system results in undesired interference and cross talk between adjacent detectors, especially when veneer is wet and connection is effectively made through conveyor ground via the wet veneer at an uncontrolled level.

SUMMARY OF THE INVENTION

According to one embodiment of the present invention, a conductive conveyor receives material such as plywood veneer and transports the same adjacent conductive transmitting and receiving plates disposed in spaced facing relation to the material. Energizing means such as a high voltage A.C. transformer provides an A.C. voltage at a transmitting plate with respect to a first potential reference and with respect to a second potential reference different from the first potential reference for normally causing an A.C. signal to be coupled along the moisture in the wood from the transmitting plate to a receiving plate or plates. A detector circuit for indicating moisture receives a moisture responsive A.C. signal as an input, e.g. by being in circuit with a said receiving plate. The circuit is returned to the first potential reference for measuring the A.C. signal, and the receiving plate or plates are preferably provided with a shielding enclosure also returned to the first potential reference. The conductive conveyor is connected to the second potential reference for providing an alternative conductive signal path to said material, effective, for example, under high moisture conditions as might otherwise shunt or eliminate the signal. Thus, a second conductive signal path is provided via the same moisture in the wood as would ordinarily cause the problem. In essence, a separate signal return is provided, but the conveyor ground path is maintained whereby a suitable voltage level can be applied to the detector even under high moisture conditions.

Preferably, a plurality of receiving plates are disposed across the path of the material, and in offset relation to the transmitting plate in the direction of material travel. The respective receiving plates operate separate detector circuits adapted to energize marking means indicative of the location of the wet material.

According to an alternative embodiment, rather than employing a transmitting plate, the second conductive signal path is relied upon for coupling a signal by means of which moisture content is ascertained. In effect, the detector circuit return and shielding enclosure means are driven with respect to the conductive conveyor, and the detector circuit provides an output only in the presence of veneer having a predetermined moisture content.

It is accordingly an object of the present invention to provide an improved moisture detector for detecting moisture in plywood veneer.

It is a further object of the present invention to provide an improved moisture detector for detecting moisture in plywood veneer and the like wherein such detector is economical in construction and reliable in operation.

It is another object of the present invention to provide an improved moisture detector for detecting moisture in plywood veneer and the like wherein the moisture detecting signal is not completely shorted out under high moisture conditions.

The subject matter which I regard as my invention is particularly pointed out and distinctly claimed in the concluding portion of this specification. The invention, however, both as to organization and method of operation, together with further advantages and objects thereof, may best be understood by reference to the following description taken in connection with the accompanying drawings wherein like reference characters refer to like elements.

DRAWINGS

DETAILED DESCRIPTION

Figure 1:
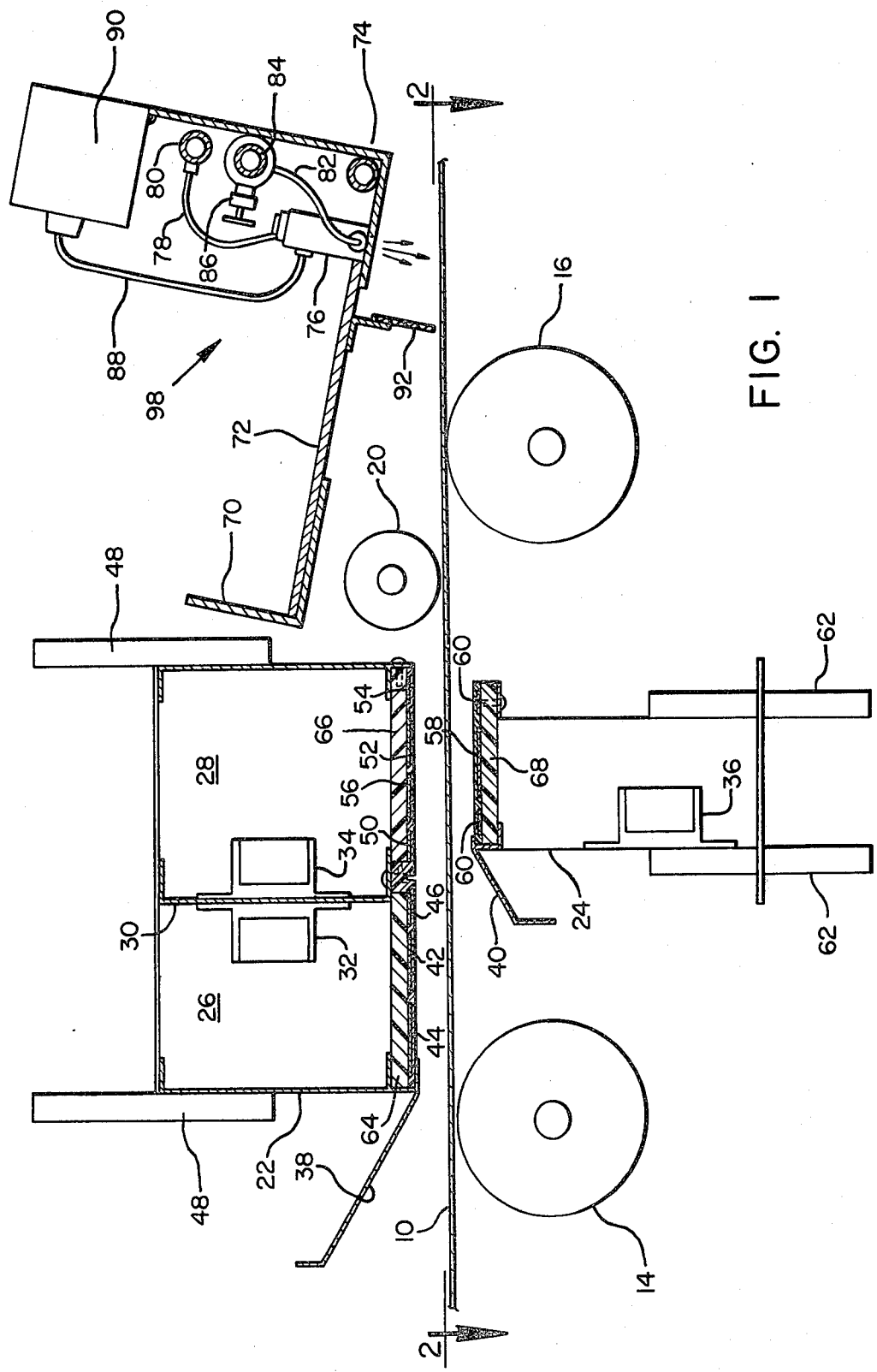
FIG. 1 is a side view of a moisture detector according to the present invention.
Figure 2:
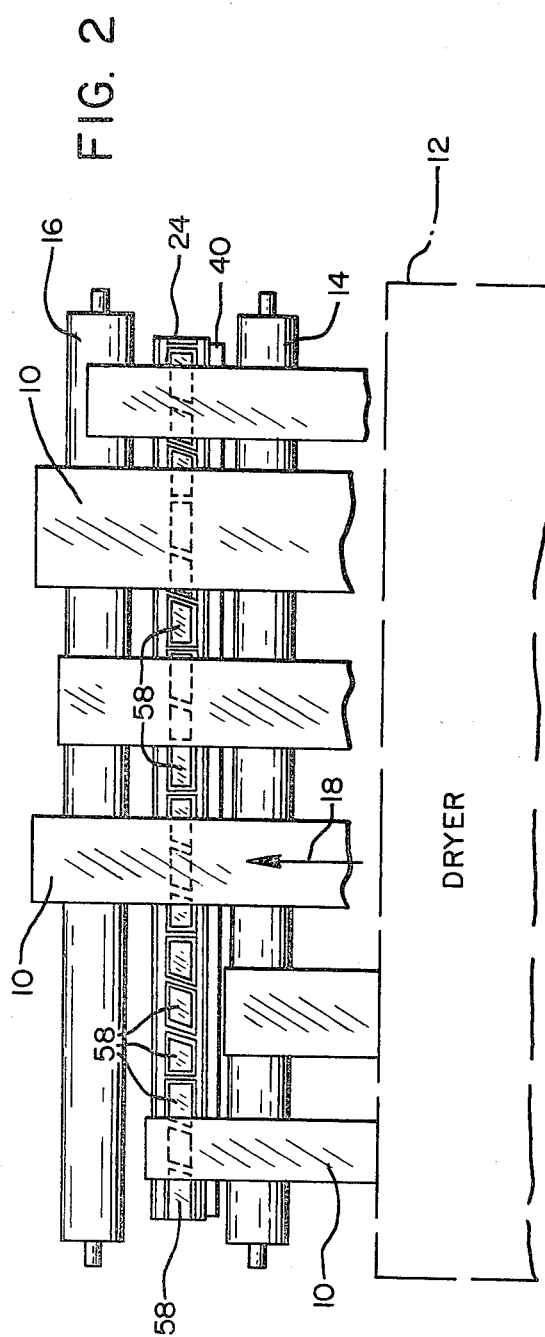
FIG. 2 is a plan view taken at 2—2 of FIG. 1 of a portion of the moisture detector.

Referring to the drawings and particularly to FIGS. 1 and 2, illustrating a first embodiment of the present invention, a plurality of veneer strips 10 are received from a veneer dryer 12 upon steel conveying system rollers 14 and 16 which are powered to move the veneer in the direction indicated by arrow 18 in FIG. 2. The veneer is received between powered rollers 14 and 16 and an upper steel roller 20 also powered for moving the veneer. The rollers 14, 16 and 20 suitably extend nearly the full width of the dryer and each one of the rollers is grounded through the conveyor frame or other machinery (not shown) which is ordinarily at earth potential.

As illustrated particularly in FIG. 1, the veneer will be guided by the conveying rollers between an upper metal cabinet 22 and a lower metal cabinet 24 housing moisture detector apparatus and providing electrical shielding. The upper cabinet 22 is divided between separate shielded compartments 26 and 28, with a dividing wall 30 therebetween supporting small heaters 32 and 34 in the respective compartments. Cabinet 24 is similarly provided with an interior heater 36. These heaters are utilized for avoiding moisture condensation on the detector surfaces as would result in false moisture indications. The heaters raise the temperature of the detector apparatus slightly above the temperature of the surroundings. A deflector 38 is attached to the forward edge of cabinet 22 and is angled upwardly, while a similar but downwardly directed deflector 40 is attached to the forward edge of cabinet 24 for further guiding the veneer and preventing damage to the detector apparatus.

On the lower side of cabinet 22 and particularly at the lower end of compartment 26, a conducting transmitting plate 42 is mounted in parallel spaced relationship to veneer strips passing therebelow. As hereinafter more fully described, the transmitting plate 42 extends substantially the full length of cabinet 22 across the path of the veneer. The transmitting plate 42 is suitably energized with an A.C. voltage as hereinafter more fully described. Positioned in parallel relation to transmitting plate 42 and spaced on either side thereof are "ground" plates 44 and 46 which also extend substantially the full length of the cabinet. These "ground" plates are insulated from the transmitting plate and are desirably connected to cabinet ground, that is to metal cabinet 22 and not to earth ground or the ground potential to which conveyor rollers 14, 16 and 20 are connected. Cabinet 22 is suspended from structure or other machinery (not shown) by insulating support plates 48. "Ground" plates 44 and 46 aid in providing a shielding function.

At the lower end of compartment 28 a further plurality of mutually insulated plates are located in parallel spaced relation to veneer strips passing thereunder. These plates include "ground" plates 50 and 52, and a test plate 54 which suitably extend in parallel relation across the full length of the cabinet. Plates 50 and 52 are connected to cabinet 22 and perform an electrical shielding function. Receiving plates 56, positioned between and insulated from ground plates 50 and 52 are separate or segmented so as to be insulated from one another along the length of the cabinet 22, i.e. across the path of veneer strips coming from the dryer. These receiving plates are approximately the same shape and configuration as receiving plates 58 which are mounted on the upper side of lower cabinet 24 in parallel and spaced relation to the passage of veneer strips, except plates 58 are slightly wider. As can be seen in FIG. 2, receiving plates 58 are segmented and extend in an aligned row substantially the full length of the cabinet 24. On either side of receiving plates 58 are located "ground" plates 60 extending the full length of cabinet 24 in spaced relation to plates 58. Plates 60 are insulated from plates 58 and "grounded" to cabinet 24 such that they provide an electrical shielding function, cabinet 24 being supported by insulating plates 62 above the level of the floor or machinery surface. Cabinets 22 and 24 are connected together to form a common reference. The transmitting and receiving plates are offset with respect to one another along the direction of travel of the veneer so that they are disposed towards at least predominantly different portions of the veneer. Corresponding and aligned receiving plates 56 and 58 are connected together, as hereinafter indicated, for detecting moisture on a given strip of veneer or in a given area thereof. As can be seen in FIG. 2, receiving plates have a length comparable to or less than the width of the veneer strips 10. Test plate 54 is used for providing a standard test signal in relatively close proximity to the receiving plates in order to check operation thereof.

Figure 4:
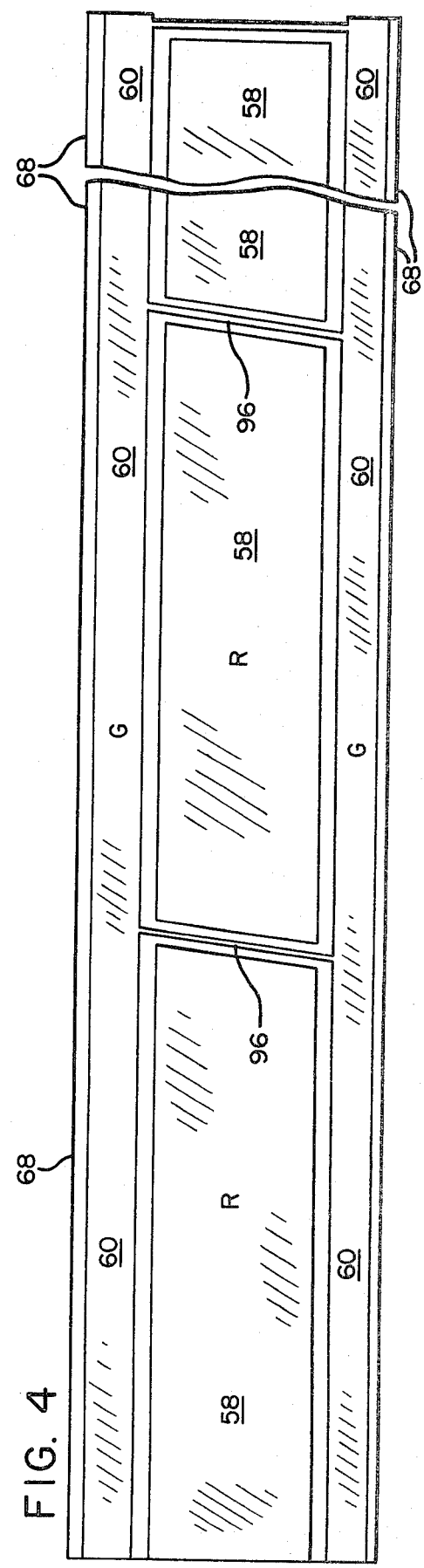
FIG. 4 is a face view of another circuit board mounting another portion of a conductive plate array according to the present invention.
Figure 3:
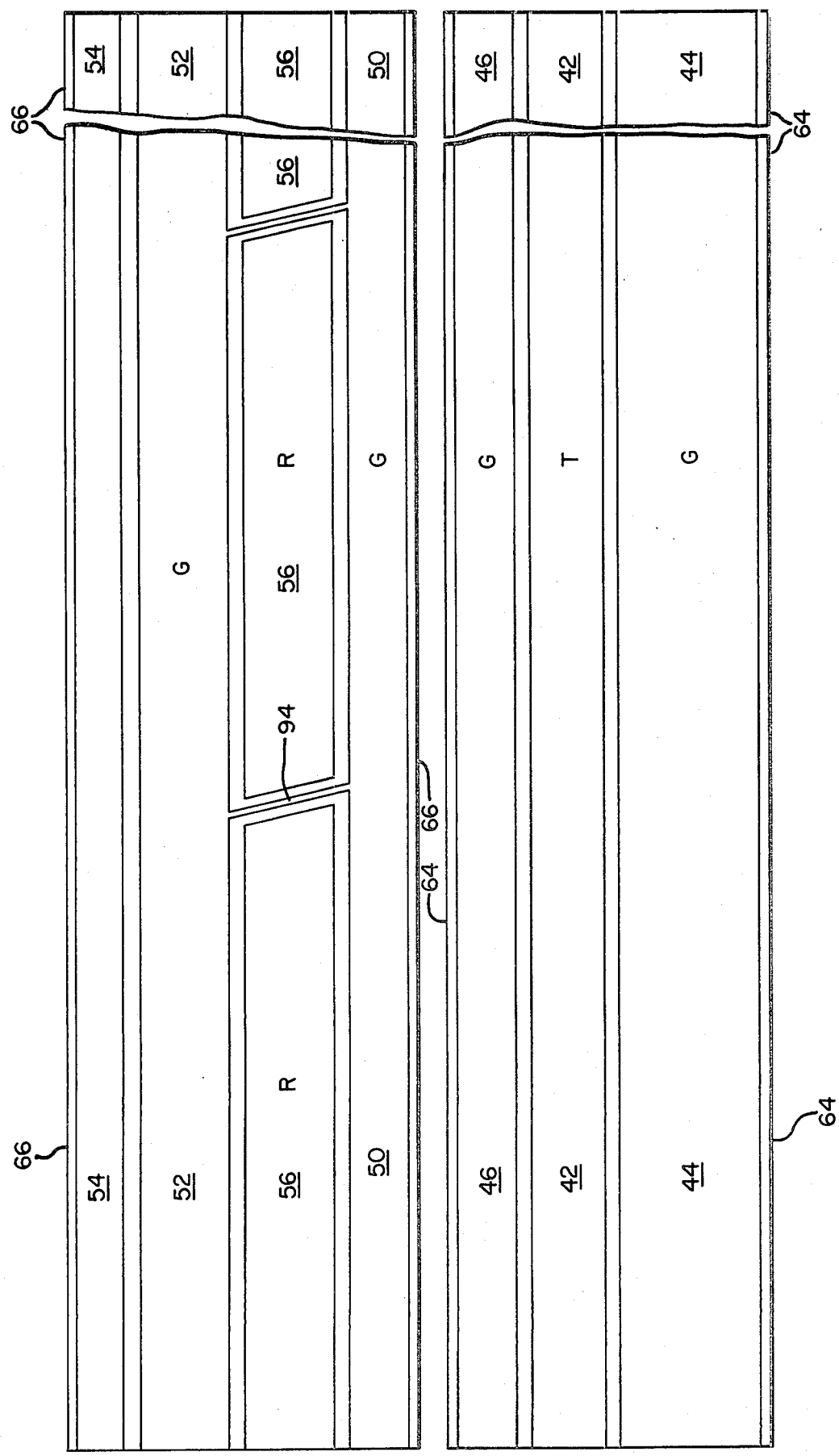
FIG. 3 is a face view of circuit boards mounting a portion of a conductive plate array according to the present invention.

The various arrays of plates suitably comprise printed or etched conductors on circuit board sections composed of epoxy glass and forming the top or the bottom of the respective cabinets. Referring to FIG. 3, typical circuit boards 64 and 66 are illustrated, which form the lower surface of cabinet 22. FIG. 4 illustrates a typical circuit board 68 which provides the upper surface of cabinet 24. FIGS. 3 and 4 each illustrate boards for one-sixth of the entire array, and it is understood a plurality of such boards placed in end-to-end arrangement and appropriately connected are therefore employed. Each board includes three receiving plates 56 or 58. As seen in FIG. 1, the respective circuit boards are suitably held in place by metal screws. The plate arrays as supported by cabinets 22 and 24 are suitably positioned about two inches apart such that the spacing between the respective plate arrays and the veneer passing therebetween is approximately three-fourths inch to one inch. As can be seen from FIG. 1, the width of the various plates is roughly comparable to the spacing between the plate arrays.

As veneer passes between the plate arrays, capacitive coupling takes place between the various plates and moisture in the veneer. The transmitting and receiving plates are isolated from one another along the veneer and separated by the metal cabinets and the "ground" plates such that an insubstantial coupling takes place directly from the transmitting plate to the receiving plates. The configuration tends to compensate for variations in thickness and positioning of the veneer. Thus, the conduction path is substantially along the moisture in the veneer and there is not as much dependence upon its thickness or position. The high voltage signal applied to the transmitting plate is capacitively coupled to moisture in the wood and along the wood, and is then capacitively coupled to a receiving plate. Detection circuitry connected to the receiving plate indicates the degree of moisture by indicating the signal level received. The "ground" plates aid in rendering the system less sensitive to position of the veneer in a vertical direction. Thus, if a sheet of veneer more closely approaches transmitting plate 42, the resultant signal tends to be "shunted out" to a greater degree to "ground" plates 44 and 46. Similarly, if the veneer should closely approach a receiving plate 56 or 58 whereby an incorrectly high indication of moisture might be given, the "ground" plates on either side thereof will tend to reduce the signal strength. Also, placing a receiving plate above as well as below the path of the veneer results in a compensating effect whereby the veneer sheet farther from a receiving plate 56 will more closely approach a receiving plate 58 in parallel electrical connection therewith such that the moisture detection signal is not greatly attenuated.

As can be seen in FIG. 3, the "ground" plates 50 and 52 are suitably extended between detector plates 56 as at 94 for isolating and shielding adjacent detector plates 56 whereby a signal on one receiving plate 56 will not be immediately coupled therefrom to the next receiving plate 56 causing an indication of moisture for an adjacent veneer strip or the like which might not, as a matter of fact, contain an objectionable moisture level. For the same reason, "ground" plates 60 are extended between detector plates 58 as shown at 96 in FIG. 4.

As hereinbefore indicated, the receiving plates 56 and 58 are segmented across the width of the conveyor system, with aligned pairs thereof providing an indication of moisture for a particular veneer sheet or portion thereon. The resulting indication can be employed for marking the veneer sheet whereby the same is easily and quickly identified by operating personnel and can be returned to the input of the dryer for redrying. In particular, a plurality of paint sprayers are employed, with one such sprayer being illustrated in FIG. 1. It is understood there will be one such sprayer positioned adjacent the output of the moisture detector apparatus for each pair of aligned and parallel connected receiving plates. A steel angle 70 extends across the apparatus above roller 20 and has an expanded metal support plate 72 secured thereto. In turn, a bracket 74 is attached to the support plate and mounted thereupon is a sprayer head 76 adapted to spray a fluid such as paint, through a matching aperture in the bottom leg of bracket 74 towards the veneer passing by roller 16.

A paint or colored fluid such as an alcohol based marking fluid is delivered to spray head 76 via tubing 78 from a pipe 80 which extends crossways of the apparatus for supplying the various spray heads. Similarly, air under pressure is supplied through tubing 82 from a pipe 84 extending across the apparatus. The air pressure can be adjusted with a valve 86. The spray head 76 is energized for operation via a control cable 88 from control box 90, the spray head suitably being of the electrically actuated solenoid type. Control box 90 distributes the electrical supply leads to the various spray heads and contains a portion of the electrical circuitry according to the present invention. When moisture is detected on a particular veneer sheet or a portion thereof, the spray head aligned with the receiving plate which detected the moisture will mark the veneer sheet so the same can be set aside for redrying and will not be used in the assembly of plywood or the like with other sheets having a lower moisture content. A strip of belting 92 is suitably disposed along and under support plate 72 immediately adjacent the spray head 76 to prevent the spray from striking roller 16 or other equipment.

Figure 5:
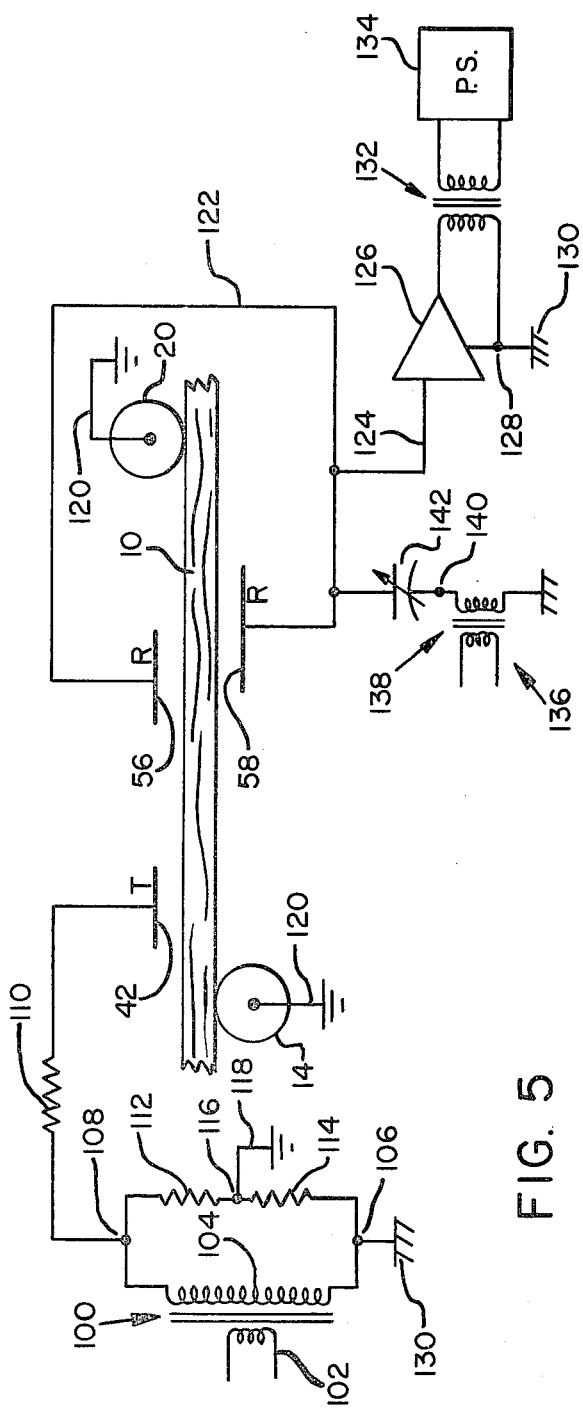
FIG. 5 is a schematic diagram of the moisture detector circuit according to the present invention.

FIG. 5 illustrates the electrical circuit of the moisture detector according to the present invention, and like elements are identified by the same reference numerals as employed in the previously described drawings. Transmitting plate 42 is energized from a transformer 100 having a primary winding 102 adapted to be connected to an alternating current power source, for example 110 volts at 60 cycles. The transformer has a high voltage secondary 104 which in the present example produces a potential of 1600 volts. The first or reference terminal 106 of the transformer is connected to a first circuit potential reference below machinery or earth ground comprising the "ground" of cabinets 22 and 24 and "ground" plates 44, 46, 50, 52 and 60, it being recalled the cabinets are insulated with respect to the machinery or earth ground. The cabinet "ground" is indicated by symbol 130. The remaining transformer terminal 108 is coupled to transmitting plate 42 through a dropping resistor 110 which suitably has a high resistance value such as 5.4 megohms. A voltage divider, comprising resistors 112 and 114 in series, is disposed between terminals 108 and 106. The resistance of resistor 112 is much larger than that of resistor 114, e.g. resistor 112 suitably has a value of 2.4 megohms while resistor 114 has a value of 150K ohms. Consequently, resistor 114 drops a voltage of about 100 volts between the tap 116 between the two resistors and terminal 106. The tap 116 between the two resistors is connected to machinery or earth ground by means of grounding lead 118. It will be recalled conveyor rollers 14 and 20 (as well as conveyor roller 16 not shown in FIG. 5) are grounded to machinery or earth ground. Machinery or earth ground comprises the second potential reference of the circuit. In FIG. 5, the rollers are illustrated as grounded by means of connections 120. However, it will be appreciated the conveyor rollers in most cases are grounded via their bearings which in turn are supported on earth grounded machinery structure (not shown).

Receiving plates 56 and 58 are illustrative of a pair of aligned receiving plates which are connected together by a lead 122, and which are also connected to input lead 124 of detector circuitry comprising amplifier 126. It is understood there is one such amplifier connected to each pair of receiving plates. The detector circuitry amplifier return or reference terminal 128 is connected to cabinet ground as indicated by symbol 130, and therefore the voltage on receiving plates 56 and 58 is measured, or provided with respect to, the cabinet ground return at terminal 128. The output of detector circuit amplifier 126 is coupled, with respect to the cabinet ground, to the primary of an isolating transformer 132 having its secondary connected in operating relation to sprayer 134. Thus, when a signal of sufficient strength is received from receiving plates 56 and 58, an amplified signal will operate the corresponding sprayer 134 and provide a mark indicating a wet sheet of veneer. The sensitivity of the amplifier is desirably adjustable by conventional means (not shown) to set a threshold for moisture detection and sprayer operation. It is understood sufficient delay is provided in the amplifier 136 and sprayer operation so that the sheet of veneer has sufficient time to move under the sprayer before the latter is actuated.

A balancing circuit 136 is also desirably connected to the input 124 of detector circuit amplifier 126. The balancing circuit includes a comparatively low voltage transformer 138 having its primary connected to a source 180 degrees out of phase with the source to which primary 102 is connected, e.g. the same 110 volt, 60 cycle supply with leads reversed. The secondary is returned to cabinet ground, while the remaining secondary terminal 140 is coupled by means of variable capacitor 142 to the input 124 of detector circuit amplifier 126. The polarity of the output of transformer 138 is such and capacitor 142 is adjusted such that in the absence of veneer, or in the presence of dry veneer, any stray signal at input lead 124 is balanced out. Thus, a voltmeter or other indicating instrument may be connected to the output of detector circuit amplifier 126, and capacitor 142 adjusted such that a sprayer would not be operated in the absence of moisture.

During operation in accordance with the present embodiment, moisture in veneer 10 will normally couple the high voltage A.C. signal on transmitting plate 42 along the veneer so the same signal is capacitively coupled to receiving plates 56 and 58 whereby the sprayer 134 will be activated for a given adjustable sensitivity of detector circuit amplifier 126. At such time, the signal voltage on transmitting plate 42 is provided with respect to cabinet ground 130, and the detector circuit amplifier is responsive to the voltage between the receiving plates and cabinet ground 130. However, as hereinbefore mentioned, the veneer can in some cases reach a moisture level such that the rollers 14 and 20 of the conveyor system would tend to short out the A.C. signal. Thus, although it is important an indication be given for a high moisture content, no output may as a matter of fact be produced. However, in accordance with the present embodiment of the invention, the conveyor system, including rollers 14 and 20 connected to earth ground, is tapped up on voltage divider 112, 114. In effect, then, rollers 14 and 20, instead of shorting out the signal, will provide a signal path along the veneer strip 10 with respect to cabinet ground under higher moisture conditions. Since tap 116 is approximately 100 volts positive with respect to terminal 106, the strip of wet veneer will have a 100 volt positive voltage level with respect to cabinet ground 130. This is quite adequate for operating detecting circuit amplifier 126 to substantially the same extent as a capacitively coupled signal from transmitting plate 42. Except for the "grounding" effect of rollers 14 and 20 at higher moisture levels, an excessively high voltage could even be received at amplifier 126, i.e. from the transmitting plate signal. However, as the veneer becomes quite wet, the voltage level is in effect reduced to 100 volts.

The resistance values of resistors 110, 112 and 114 are very high and act as dropping resistors in case inadvertent body contact is made with the transmitting plate 42 or cabinet ground 130. If body contact is inadvertently made with transmitting plate 42, resistor 110 drops substantially all the high voltage of the transformer secondary. Similarly, should body contact be made with the insulated cabinets 22 and 24 which are normally at a 100 volt level with respect to earth ground, dropping resistor 112 will drop substantially the entire transformer secondary voltage thereby providing protection. It will be observed high voltage terminal 108 has the same polarity with respect to the first potential reference provided at terminal 106 and the second potential reference provided at tap 116. Also, the A.C. signal received at input 124 of amplifier 126 has the same instantaneous polarity as the A.C. voltage at transformer terminal 108 and transmitting plate 42 with respect to both the first potential reference i.e. cabinet ground, and with respect to the second potential reference, i.e. earth ground. Furthermore, earth ground is placed at a higher potential level in the system than the cabinet grounds. Consequently, the presence of moisture is easily measured by a single amplifier 126 throughout the moisture range for each pair of receiving plates substantially in line with a corresponding sprayer.

Figure 6:
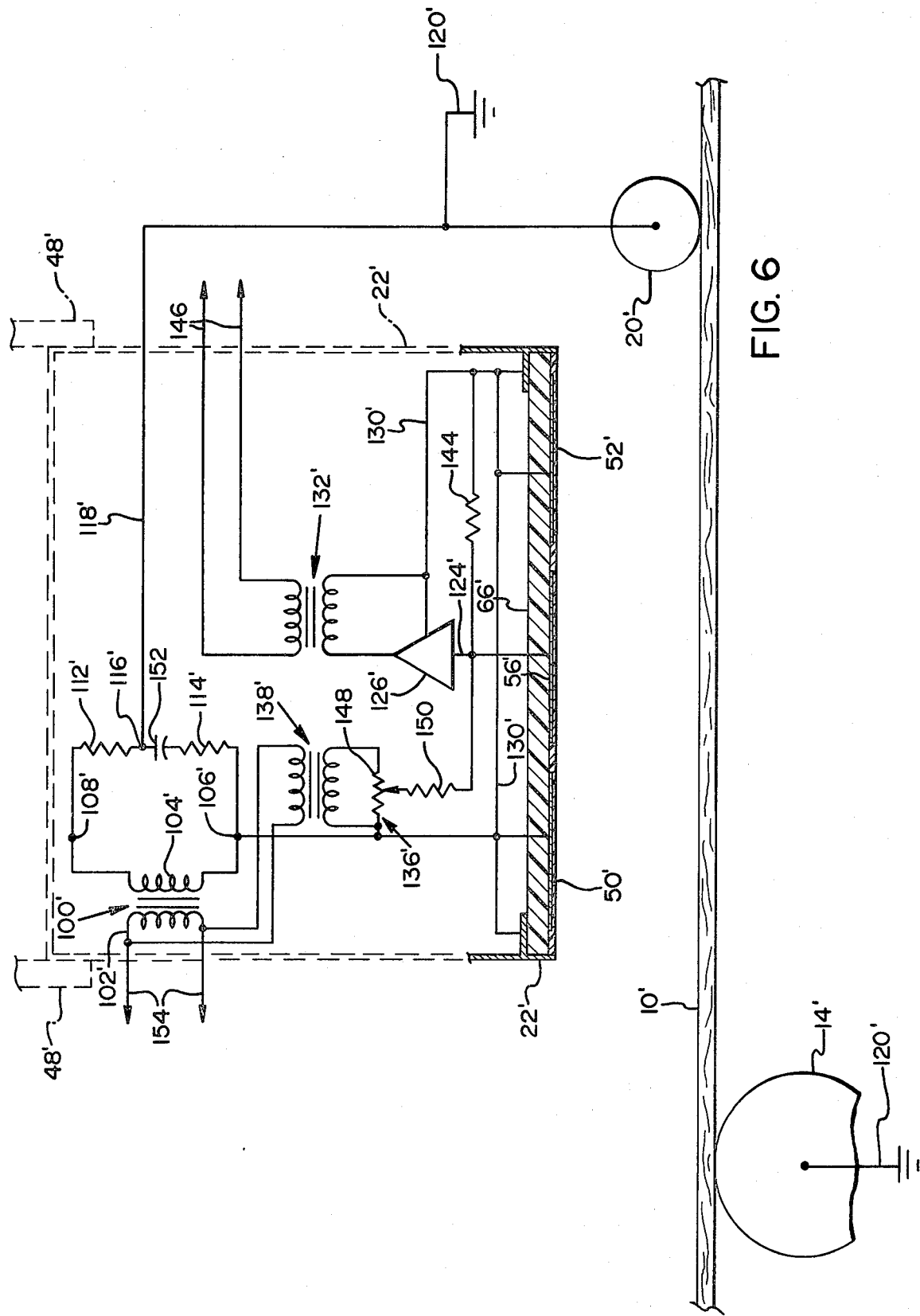
FIG. 6 is a partially schematic illustration of a moisture detector according to a second embodiment of the present invention.

While the embodiment of the present invention as just described has found considerable utility for moisture detection purposes, in most cases very satisfactory moisture detection is accomplished according to a second embodiment of the present invention. The second embodiment is substantially similar to the first except the transmitting plate 42 is deleted and the moisture path in the material through earth ground via the grounded rollers of the conveyor is relied upon for moisture detection. This embodiment is more particularly illustrated, partially schematically, in FIG. 6, wherein reference numerals are primed to indicate elements substantially similar to those in the previous embodiment. Again, veneer strips 10' are received upon a conductive conveyor including steel rollers 14' and 20' which are grounded through the conveyor frame whereby they are at electrical earth potential. The veneer will be guided by the conveyor past the metal enclosure cabinet 22' housing moisture detector apparatus and providing electrical shielding. The cabinet may also be supplied with an interior heater as in the previous embodiment.

On the lower side of metal enclosure cabinet 22' there is mounted a receiving plate 56' as well as "ground" plates 50' and 52' on either side of the receiving plate along the direction of travel of veneer 10'. These "ground" plates are insulated from the receiving plate and are connected to cabinet ground, that is to the metal enclosure cabinet 22' via connection 130', and not to earth ground or the ground potential to which the conveyor rollers are connected. These "ground" plates aid in providing a shielding function as hereinafter more fully discussed. The plates 56', 50' and 52' suitably comprise printed or etched conductors on circuit board 66' composed of epoxy glass an forming the lower surface of cabinet 22'. The cabinet 22' is suspended from structure or other machinery by insulating support plates 48' so as to position the cabinet 22' including the plates 50', 56' and 52' in parallel spaced relationship to veneer strip 10' passing therebelow. The spacing between the plates and the veneer passing thereunder is suitably approximately three-fourths of an inch to 2 inches. It will be understood the plates illustrated in FIG. 6 suitably form part of an array as in the previous embodiment extending across the width of the conveyor system. The receiving plates in such array are segmented to detect moisture at different locations, while the "ground" plates need not be segmented, being connected to the cabinet ground.

The width of the various plates can be roughly comparable to the spacing between the plates and the veneer 10', while the spacing of the plates from each other along the lower side of cabinet 22', as well as the spacing of the ground plates from the lower edges of cabinet 22', is suitably a fraction of that distance. Furthermore, since "ground" plates 50' and 52' are connected to the cabinet 22', they may extend to the lower cabinet edges. The receiving plate 56' is desirably offset along the veneer 10' from the location of conveyor rollers such as indicated at 14' and 20'.

The moisture detector circuit apparatus within shielding cabinet 22' principally includes amplifier 126' receiving an input 124' from receiving plate 56', the amplifier 126' being returned to cabinet ground via connection 130' to which amplifier input resistor 144 is also returned. The output of amplifier 126' is coupled, with respect to cabinet ground, to the primary of an isolating transformer 132' having secondary connections 146 connected in operating relation with an appropriate paint sprayer or the like.

A balancing circuit 136' is also desirably connected to the input 124' of the detector circuit amplifier 126'. The balancing circuit includes a low voltage transformer 138', the secondary of which is returned to cabinet ground via connection 130'. Other phase shift networks may also be used. A potentiometer 148 is disposed across the transformer secondary and the movable tap of the potentiometer is connected to amplifier input 124' by means of coupling resistor 150. The polarity of the output of transformer 138' is such and potentiometer 148 is adjusted such that in the absence of veneer, or in the presence of dry veneer, any stray signal at input 124' is balanced out. Thus, potentiometer 148 is adjusted such that a paint sprayer would not be operated in the absence of moisture.

As hereinbefore indicated, a high voltage transmitting plate is not utilized in this embodiment, and consequently a high voltage energizing means for the transmitting plate is likewise not required. The energizing means comprises a transformer 100' having a primary 102' adapted to be connected to an alternating current source via leads 154. The secondary winding need not produce a high voltage, and as a matter of fact the transformer may suitably comprise a step down transformer for providing an output on the order of 50 to 100 volts. The first terminal or reference point 106' is connected to cabinet ground via connection 130', it being recalled the cabinet is insulated with respect to the machinery or earth ground. A voltage divider, comprising resistor 112', capacitor 152 and resistor 114' is disposed between the remaining terminal 108' of the transformer and the reference terminal 106'. The tap 116' between resistor 112' and capacitor 152 comprises a second potential reference point and is connected to machinery or earth ground 120' by means of grounding lead 118'. Thus, potential point 118' is connected to the conveyor rollers, e.g. rollers 14' and 20' in FIG. 6 as well as other grounded metal rollers which may comprise the conveyor. The second potential point is identical to machinery or earth ground.

Resistors 112' and 114' both have relatively large resistance values although the impedance of resistor 114' in series with capacitor 152 is higher than that of resistor 112' whereby a large proportion of secondary voltage normally appears between terminals 116' and 106'. Nevertheless, should inadvertent body contact be made with the insulated cabinet 22', dropping resistor 112' will provide protection by dropping most of the transformer secondary voltage.

During operation, according to this embodiment, signal voltage with respect to cabinet ground 130' is provided on grounded rollers 14' and 20', and these rollers effectively make contact with moisture in veneer 10'. A signal path in the veneer is thus completed from the rollers to the moisture and longitudinally along the moisture in the veneer to the vicinity of receiving plate 56'. Plate 56' is capacitively coupled to the moisture in the veneer and provides an input signal to amplifier 126' with respect to cabinet ground. Thus, again, instead of shorting out the signal, the grounded conveyor forms part of the signal path.

The metal enclosure cabinet 22' and the plates 50' and 52' on either side of the receiving plate 56' provide shielding, not only for the detector circuit within the cabinet but also for the receiving plate itself. The cabinet 22' as well as plates 50' and 52' are in effect driven by the alternating current signal input at an A.C. voltage between approximately 50 and 100 volts, while the reference return or ground return of amplifier 126' is similarly driven. Since the input environment of the receiving plate varies with the alternating current signal, and since the input terminal 124' of the amplifier, connected between registors 150 and 144, normally moves up and down with the alternating current signal, no input signal is normally provided with respect to the amplifier reference, and no output is normally produced for operating a paint sprayer or the like. The shielding cabinet 22' and the plates 50' and 52' shield the amplifier input from external bodies which do not have the same alternating current reference. The amplifier input will be substantially shielded from and unaffected by external earth grounded structures not in the direct vicinity of receiving plate 56', and will also not be affected by a completely insulated body or dry veneer 10 adjacent receiving plate 56'. However, if the veneer 10' directly adjacent receiving plate 56' is wet, forming part of a path to grounded rollers 14' and 20', the capacitive coupling to receiving plate 56' will cause a signal level to appear at the input 124' of amplifier 126' with respect to cabinet ground 130', thereby causing the amplifier to detect the moisture in the veneer and supply an output at 146 for operating a corresponding paint sprayer. As in the previous embodiment, the plates 50' and 52' not only provide shielding but also aid in rendering the system somewhat less sensitive to position of the veneer in a vertical direction. Thus, as the veneer moves closer to the receiving plate 56', the "ground" plates 50' and 52' on either side thereof have a partial shunting effect due to the capacitive coupling, or viewed another way, these plates couple the cabinet reference into moisture in the wood and partially compensate for variations in veneer position.

As in the previous embodiment, separate sprayers are suitably coupled to plural amplifiers via terminals 146 which receive inputs from different segmented receiving plates. Therefore, a paint sprayer will mark a portion of the veneer in substantial alignment with the moisture detected. The sensitivity of the amplifiers is desirably adjusted by conventional means (not shown) to set a threshold for moisture detection and sprayer operation. It is again understood sufficient delay is provided in the amplifier and paint sprayer operation so that the sheet of veneer has sufficient time to move under the sprayer before the latter is actuated.

While I have shown and described plural embodiments of my invention, it will be apparent to those skilled in the art that many changes and modifications may be made without departing from my invention in its broader aspects. I therefore intend the appended claims to cover all such changes and modifications as fall within the true spirit and scope of my invention.

I claim:

1. Apparatus for detecting the moisture content of material comprising:
    a conductive conveyor for receiving said material and transporting the same in a first direction, conductive transmitting and receiving plates disposed in spaced facing relation to said material on said conveyor and in spaced relation to one another for respectively providing capacitive coupling to moisture in said material, energizing means coupled to said transmitting plate for providing an A.C. voltage at said transmitting plate with respect to a first potential reference and with respect to a second potential reference different from the first potential reference for normally causing an A.C. signal to be coupled from said transmitting plate to and along moisture as may be present in said material to said receiving plate, a detector circuit for indicating moisture in said material, said detector circuit receiving an A.C. signal input from moisture in said material via said receiving plate, said detector being returned to said first potential reference for measuring said signal with respect to said first potential reference, said signal normally having the same polarity as said A.C. voltage with respect to both said first potential reference and said second potential reference, and means for connecting said conductive conveyor to said second potential reference to provide an alternative conductive signal path to said material under high moisture conditions to prevent said conveyor from eliminating signal coupling via moisture in said material under high moisture conditions.

2. The apparatus according to claim 1 wherein said conductive plates are disposed in offset relation to one another along said first direction so that each plate is disposed toward at least a predominantly different portion of said material with the major electrical path between said plates extending along said material.

3. The apparatus according to claim 1 wherein the voltage between said transmitting plate and said first potential reference is higher than the voltage between said transmitting plate and said second potential reference.

4. The apparatus according to claim 1 wherein said second potential reference comprises ground potential.

5. The apparatus according to claim 1 wherein both said conductive plates are disposed on a first side of said material.

6. The apparatus according to claim 5 further including a second receiving plate disposed on the opposite side of said material from said transmitting and receiving plates and also being connected to said input of said detector circuit.

7. The apparatus according to claim 1 wherein said conductive plates are disposed on opposite sides of said material.

8. The apparatus according to claim 1 wherein said conductive conveyor comprises grounded metal rollers for receiving plywood veneer material.

9. The apparatus according to claim 1 further including additional receiving plates disposed across said conveyor, with separate detector circuits connected respectively to the additional receiving plates.

10. The apparatus according to claim 1 wherein said means for energizing said transmitting plate comprises a transformer having a winding with a first terminal coupled to said transmitting plate and means coupled to said winding for providing said first potential reference and said second potential reference.

11. The apparatus according to claim 10 wherein said means coupled to said winding for providing said first potential reference and said second potential reference includes a voltage divider interposed between said first terminal and another terminal on said winding where said first potential reference is derived, and a tap on said voltage divider for providing said second potential reference.

12. Apparatus for detecting the moisture content of material comprising:
conductive conveyor means for receiving said material and moving the same in a first direction,
a first conductor plate disposed in spaced facing relation to said material, and a plurality of second conductor plates disposed in spaced facing relation to said material in offset relation to the first conductor plate along said first direction so the major electrical path between said first conductor plate and each of said second conductor plates extends substantially along said material, said second conductor plates being positioned in locations spaced substantially across the path of said material as it moves in said first direction,
energizing means coupled to said first plate for providing a voltage at said first plate with respect to a first reference potential reference and with respect to a second potential reference,
detector circuits coupled to receive their respective inputs from the second conductor plates with respect to said first potential reference, each said detector circuit indicating moisture in said material substantially adjacent the second conductor plate to which the detector circuit is coupled,
and means connecting said conductive conveyor means to said second potential reference.

13. The apparatus according to claim 12 wherein said second potential reference comprises ground potential.

14. The apparatus according to claim 12 wherein said means for energizing said first conductor plate comprises a transformer having a winding with a first terminal coupled to said first conductor plate, and means coupled to said winding for providing said first potential reference and said second potential reference.

15. The apparatus according to claim 14 wherein said means coupled to said winding for providing said first potential reference and said second potential reference includes a voltage divider interposed between said first terminal and another terminal on said winding where said first potential reference is derived, and a tap on said voltage divider for providing said second potential reference.

16. The apparatus according to claim 12 further including a plurality of sprayers positioned adjacent said conveyor means and energized respectively by said detector circuits, each of said sprayers being located substantially in line with a respective second conductor plate for marking said material in response to detection of moisture adjacent a said second plate.

17. The apparatus according to claim 12 including additional plates also disposed in spaced facing relation to said material, said additional plates being located adjacent said first and second conductor plates and being connected to said first potential reference.

18. The apparatus according to claim 12 including metal enclosures supporting said first and second conductor plates, said energizing means, and detector circuits, said metal enclosures being returned to said first potential reference.

19. The apparatus according to claim 12 further including a balancing circuit for applying a potential to said input of a said detector circuit for balancing out the input of said detector circuit in the absence of moisture in said material.

20. The apparatus according to claim 19 wherein said balancing circuit comprises a transformer having a winding returned to said first potential reference, and a variable capacitor coupling said winding to said input of said detector.

21. The apparatus according to claim 12 including dropping resistor means coupling said energizing means to said first plate.

22. Apparatus for detecting the moisture content of material comprising:
   a conductive conveyor for receiving said material and transporting the same in a first direction,
   first and second conductive plates disposed in spaced facing relation to said material on said conveyor and in offset relation to one another along said first direction for respectively providing capacitive coupling to moisture in said material,
   A.C. voltage source means providing an A.C. voltage connected to produce an alternating current signal along a circuit path including said plates and via capacitive coupling to said moisture in said material,
   detector means responsive to the alternating current signal in said circuit path for determining the moisture content according to the conductivity of said circuit path,
   a return path for completing a circuit to said source means at a potential reference differing from that of said conductive conveyor,
   and means for connecting said conductive conveyor to a second potential reference at said source means different from the A.C. voltage of said source means and said return path.

23. The apparatus according to claim 22 wherein said conductive conveyor comprises grounded metal rollers for receiving plywood veneer material.

24. The apparatus according to claim 22 further including additional plates disposed across said conveyor means with separate detector means connected thereto for indicating moisture at various locations across said conveyor.

25. Apparatus for detecting the moisture content of material comprising:
   a conductive conveyor for receiving said material and transporting the same in a first direction,
   energizing means for providing a signal voltage difference between a first potential point and a second potential point with respect to said first potential point,
   means for connecting said conductive conveyor to said second potential point to provide a signal path to moisture in said material received and transported by said conveyor,
   conductive receiving plate means disposed in spaced facing relation to said material on said conveyor for providing capacitive coupling to moisture in said material,
   and a detector circuit for indicating moisture in said material, said detector circuit receiving an input from moisture in said material via said receiving plate means, said detector circuit being returned to said first potential point as a reference.

26. The apparatus according to claim 25 wherein said detector circuit comprises an amplifier circuit having its input coupled to said receiving plate means, said amplifier circuit being returned to said first potential point as a reference potential.

27. The apparatus according to claim 25 including shielding means adjacent said conductive receiving plate means in spaced relation to said material on said conveyor, said shielding means being connected to said first potential point.

28. The apparatus according to claim 27 wherein said shielding means comprises a cabinet enclosing said detector circuit.

29. The apparatus according to claim 28 wherein said shielding means further comprises conductive plate means adjacent said conductive receiving plate means and connected to said cabinet.

30. The apparatus according to claim 29 wherein said detector circuit comprises an amplifier circuit having its input coupled to said receiving plate means, said amplifier circuit being returned to said first potential point as a reference potential.

31. The apparatus according to claim 25 including a metal enclosure supporting said conductive receiving plate means while being insulated therefrom, said enclosure being returned to said first potential point and receiving said detector circuit.

32. The apparatus according to claim 31 wherein said detector circuit comprises an amplifier circuit having its input coupled to said receiving plate means, said amplifier circuit being returned to said first potential point as a reference potential.

33. The apparatus according to claim 31 including conductive plate means adjacent said conductive receiving plate means in spaced relation to said material on said conveyor and connected to said metal enclosure.

34. The apparatus according to claim 25 wherein said conductive conveyor comprises grounded metal rollers for receiving plywood veneer material.

35. The apparatus according to claim 25 further including additional receiving plate means disposed across said conveyor, the separate detector circuits connected respectively to the additional receiving plate means.

36. The apparatus according to claim 25 further including a balancing circuit for applying a potential to the input of said detector circuit for balancing out the input of said detector circuit in the absence of moisture in said material.

37. Apparatus for detecting the moisture content of material comprising:
   conductive conveyor means for receiving said material and moving the same in a first direction,
   energizing means for providing a signal voltage difference between a first potential point and a second potential point with respect to said first potential point,
   means for connecting said conductive conveyor means to said second potential point to provide a signal path to moisture in said material received and transported by said conveyor,
   a plurality of conductive receiving plate means disposed in spaced facing relation to said material for providing capacitive coupling to moisture in said material, said conductive receiving plate means being positioned in locations spaced substantially across the path of said material as it moves in said first direction,
   and a plurality of detector circuits coupled to receive respective inputs from said conductive receiving plate means with respect to said first potential point to which said detector circuits are returned as a reference, each said detector circuit indicating moisture in said material substantially adjacent the conductive receiving plate means to which the detector circuit is coupled.

38. The apparatus according to claim 37 wherein said second potential point comprises earth ground potential.

39. The apparatus according to claim 37 further including a plurality of sprayers positioned adjacent said conveyor means and energized respectively by said detector circuits, each of said sprayers being located substantially in line with respect to said receiving plate means for marking said material in response to detection of moisture adjacent a said receiving plate means.

40. The apparatus according to claim 37 including shielding means adjacent said conductive receiving plate means in spaced relation to said material on said conveyor means, said shielding means being connected to said first potential point.

41. The apparatus according to claim 40 wherein said shielding means comprises metal enclosure means enclosing said detector circuits.

42. The apparatus according to claim 41 wherein said shielding means further comprises conductive plate means adjacent said conductive receiving plate means and connected to said enclosure means.

* * * * *

UNITED STATES PATENT AND TRADEMARK OFFICE
CERTIFICATE OF CORRECTION

PATENT NO. : 4,377,783
DATED : March 22, 1983
INVENTOR(S) : DELMER W. WAGNER

It is certified that error appears in the above-identified patent and that said Letters Patent is hereby corrected as shown below:

Column 8, line 43, "an" should have read --and--.

Column 14, line 40, "the" should have read --with--.

Signed and Sealed this

Ninth Day of August 1983

[SEAL]

Attest:

GERALD J. MOSSINGHOFF

Attesting Officer     Commissioner of Patents and Trademarks